United States Patent
Bathija

(10) Patent No.: US 12,332,230 B2
(45) Date of Patent: Jun. 17, 2025

(54) PREDICTION OF CEMENT LONGEVITY USING DIGITAL CEMENT MODELING

(71) Applicant: ARAMCO SERVICES COMPANY, Houston, TX (US)

(72) Inventor: Arpita P. Bathija, Houston, TX (US)

(73) Assignee: SAUDI ARABIAN OIL COMPANY, Dhahran (SA)

( * ) Notice: Subject to any disclaimer, the term of this patent is extended or adjusted under 35 U.S.C. 154(b) by 330 days.

(21) Appl. No.: 18/046,079

(22) Filed: Oct. 12, 2022

(65) Prior Publication Data
US 2024/0125755 A1    Apr. 18, 2024

(51) Int. Cl.
| | |
|---|---|
| G01N 33/24 | (2006.01) |
| E21B 47/005 | (2012.01) |
| E21B 49/00 | (2006.01) |
| G01N 23/046 | (2018.01) |
| G01N 33/38 | (2006.01) |
| G06F 30/13 | (2020.01) |
| G06F 30/20 | (2020.01) |

(52) U.S. Cl.
CPC ........... *G01N 33/24* (2013.01); *E21B 47/005* (2020.05); *E21B 49/00* (2013.01); *G01N 23/046* (2013.01); *G01N 33/383* (2013.01); *G06F 30/13* (2020.01); *G06F 30/20* (2020.01); *G01N 2223/616* (2013.01)

(58) Field of Classification Search
CPC .... E21B 47/005; G01N 23/046; G01N 33/24; G01N 33/383
See application file for complete search history.

(56) References Cited

U.S. PATENT DOCUMENTS

| | | |
|---|---|---|
| 10,197,549 B2 | 2/2019 | Thomas et al. |
| 10,830,713 B2 | 11/2020 | Zhang |

(Continued)

FOREIGN PATENT DOCUMENTS

| | | | |
|---|---|---|---|
| CN | 105487121 A | * | 4/2016 |
| JP | 2006-159221 A | | 6/2006 |

(Continued)

OTHER PUBLICATIONS

Translation of CN-105487121-A (Year: 2016).*

(Continued)

*Primary Examiner* — David P Porta
*Assistant Examiner* — Casey Bryant
(74) *Attorney, Agent, or Firm* — Osha Bergman Watanabe & Burton LLP

(57) ABSTRACT

A method to perform a field operation with digital cement modeling is disclosed. The method includes acquiring computed tomography (CT) scan data of a metal-cement core sample and a cement-rock core sample that are associated with a borehole setup, generating, based on the CT scan data of the metal-cement core sample and the cement-rock core sample, a three-dimensional (3D) image of a synthesized metal, cement, and rock core sample, generating, by at least upscaling the synthesized metal, cement, and rock core sample, a multi-scale borehole digital model of the borehole setup, and calculating, using the multi-scale borehole digital model of the borehole setup and based on digital rock physics techniques, a predicted cement longevity.

20 Claims, 6 Drawing Sheets

(56) References Cited

U.S. PATENT DOCUMENTS

| | | | |
|---|---|---|---|
| 2015/0218930 A1* | 8/2015 | Zeroug | E21B 47/005 367/30 |
| 2023/0287766 A1* | 9/2023 | Jin | E21B 41/00 |
| 2024/0125755 A1* | 4/2024 | Bathija | G01N 33/24 |
| 2024/0263553 A1* | 8/2024 | Holt | E21B 47/022 |

FOREIGN PATENT DOCUMENTS

| | | |
|---|---|---|
| WO | 9505350 A1 | 2/1995 |
| WO | 2016/018672 A1 | 2/2016 |
| WO | 2021/087154 A1 | 5/2021 |

OTHER PUBLICATIONS

Liu, T. et al.; "Digital concrete modelling: An alternative approach to microstructural pore analysis of cement hydrates"; Construction and Building Materials 303 (2021) 124558, Aug. 11, 2021 (9 pages).

Kong, W. et al.; "Research progress on cement-based materials by X-ray computed tomography"; International Journal of Pavement Research and Technology, Sep. 12, 2020 (11 pages).

Zhang, M. et al.; "Micromechanical modelling of deformation and fracture of hydrating cement paste using X-ray computed tomography characterization"; Composites Part B (2016), pp. 64-72, Nov. 5, 2015 (9 pages).

Andrä, H. et al.; "Digital rock physics benchmarks—Part II: Computing effective properties: Computers and Geosciences", vol. 50, pp. 33-43, Jan. 2013 (11 pages) doi:https://doi.org/10.1016/j.cageo.2012.09.008.

Sengupta, M. et al.; "Digital rock physics for elastic characterization of organic-rich source rocks"; SEG Technical Program Expanded Abstracts 2020, Society of Exploration Geophysicists; pp. 2510-2514 (5 pages) doi: https://library.seg.org/doi/abs/10.1190/segam2020-3423839.1.

* cited by examiner

PREDICTION OF CEMENT LONGEVITY USING DIGITAL CEMENT MODELING

BACKGROUND

Cementing is a primary component of oil well drilling, operation, and abandonment. Cement is injected into the annular space between an oil well casing and surrounding rock formations. Cement may also be used as one or more components of a plug to seal a well during abandonment. Cement failure may result in leakage of liquids from the producing well or abandoned well contributing to lost production and wellbore repair expenses. Laboratory testing of cement specimen in a tri-axial cell under confining pressure is routinely performed to measure the material properties such as Young's modulus, Poisson's ratio, and compressive strengths of the cement sheath. However, whether the measured properties meet the longevity requirement for long term zonal isolation of the well is unknown.

A digital rock is a rock model for performing non-destructive, reproducible numeric experiments to understand controlling factors in the physical and chemical processes of the rocks. The digital rock is constructed based on 2-dimensional (2D) and/or 3-dimensional (3D) rock images, such as thin-section images, SEM, XRF, XRD, slapped core photograph, CT-scan, FIB-SEM, etc. The main objective of acquiring these images is to resolve the pore structure and heterogeneity of the rock at different scales in order to extract meaningful information of the rock for running numerical simulations.

Digital rock physics (DRP) combines microtomographic imaging with advanced numerical simulations of effective material properties. DRP complements laboratory investigations to gain a deeper understanding of relevant physical processes related to transport and effective mechanical properties of the rock.

SUMMARY

In general, in one aspect, the invention relates to a method to perform a field operation with digital cement modeling. The method includes acquiring computed tomography (CT) scan data of a metal-cement core sample and a cement-rock core sample that are associated with a borehole setup, generating, based on the CT scan data of the metal-cement core sample and the cement-rock core sample, a three-dimensional (3D) image of a synthesized metal, cement, and rock core sample, generating, by at least upscaling the synthesized metal, cement, and rock core sample, a multi-scale borehole digital model of the borehole setup, and calculating, using the multi-scale borehole digital model of the borehole setup and based on digital rock physics techniques, a predicted cement longevity.

In general, in one aspect, the invention relates to a data gathering and analysis system. The data gathering and analysis system includes a data storage device for storing computed tomography (CT) scan data of core samples, core sample images, and borehole digital models, a computer processor, and memory storing instructions, when executed, causing the computer processor to acquire the CT scan data of a metal-cement core sample and a cement-rock core sample that are associated with a borehole setup, generate, based on the CT scan data of the metal-cement core sample and the cement-rock core sample, a three-dimensional (3D) image of a synthesized metal, cement, and rock core sample, generate, by at least upscaling the synthesized metal, cement, and rock core sample, a multi-scale borehole digital model of the borehole setup, and calculate, using the multi-scale borehole digital model of the borehole setup and based on digital rock physics techniques, a predicted cement longevity.

In general, in one aspect, the invention relates to a system. The system includes a wellsite having a borehole penetrating a subterranean formation in a field, and a data gathering and analysis system comprising a processor with functionality for acquiring computed tomography (CT) scan data of a metal-cement core sample and a cement-rock core sample that are associated with a borehole setup, generating, based on the CT scan data of the metal-cement core sample and the cement-rock core sample, a three-dimensional (3D) image of a synthesized metal, cement, and rock core sample, generating, by at least upscaling the synthesized metal, cement, and rock core sample, a multi-scale borehole digital model of the borehole setup, and calculating, using the multi-scale borehole digital model of the borehole setup and based on digital rock physics techniques, a predicted cement longevity, wherein the predicted cement longevity is used to perform a field operation in the borehole.

Other aspects and advantages of the claimed subject matter will be apparent from the following description and the appended claims.

BRIEF DESCRIPTION OF DRAWINGS

Specific embodiments of the disclosed technology will now be described in detail with reference to the accompanying figures. Like elements in the various figures are denoted by like reference numerals for consistency.

DETAILED DESCRIPTION

In the following detailed description of embodiments of the disclosure, numerous specific details are set forth in order to provide a more thorough understanding of the disclosure. However, it will be apparent to one of ordinary skill in the art that the disclosure may be practiced without these specific details. In other instances, well-known features have not been described in detail to avoid unnecessarily complicating the description.

Throughout the application, ordinal numbers (for example, first, second, third) may be used as an adjective for an element (that is, any noun in the application). The use of ordinal numbers is not to imply or create any particular ordering of the elements nor to limit any element to being only a single element unless expressly disclosed, such as using the terms "before", "after", "single", and other such terminology. Rather, the use of ordinal numbers is to distinguish between the elements. By way of an example, a first element is distinct from a second element, and the first element may encompass more than one element and succeed (or precede) the second element in an ordering of elements.

In general, embodiments of the invention include systems and methods for performing a field operation as facilitated by digital cement modeling. The field operation refers to physical activities performed in the field, such as an oil or gas field. In one or more embodiments of the invention, computed tomography (CT) scan data are acquired of a metal-cement core sample and a cement-rock core sample that are associated with a borehole setup. Based on the CT scan data of the metal-cement core sample and the cement-rock core sample, a three-dimensional (3D) image of a synthesized metal, cement, and rock core sample is generated. Further, by at least up scaling the synthesized metal, cement, and rock core sample, a multi-scale borehole digital model of the borehole setup is generated. A predicted cement longevity is then generated by applying digital rock physics (DRP) techniques to the multi-scale borehole digital model under the operating condition of the borehole setup. To facilitate the field operation, contents of metal material, cement material, rock material, and the operating condition of the borehole setup are varied to optimize the predicted cement longevity.

Figure 1A:
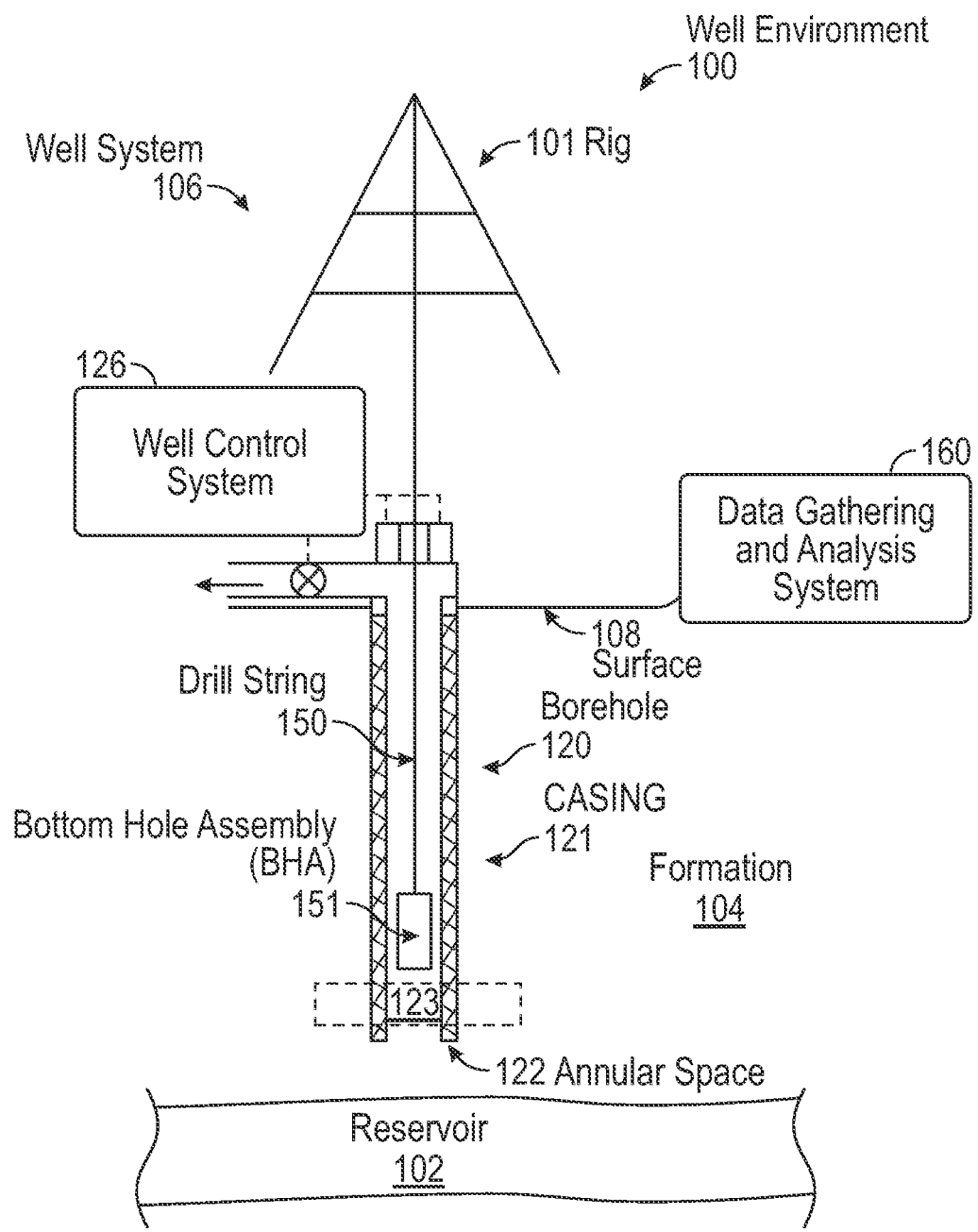
FIGS. 1A-1B show a system in accordance with one or more embodiments.

FIG. 1A shows a schematic diagram of a well environment in accordance with one or more embodiments. In one or more embodiments, one or more of the modules and/or elements shown in FIG. 1A may be omitted, repeated, and/or substituted. Accordingly, embodiments disclosed herein should not be considered limited to the specific arrangements of modules and/or elements shown in FIG. 1A.

As shown in FIG. 1A, a well environment (100) includes a subterranean formation ("formation") (104) and a well system (106). The formation (104) may include a porous or fractured rock formation that resides underground, beneath the earth's surface ("surface") (108). The formation (104) may include different layers of rock having varying characteristics, such as varying degrees of permeability, porosity, capillary pressure, and resistivity. In the case of the well system (106) being a hydrocarbon well, the formation (104) may include a hydrocarbon-bearing reservoir (102). In the case of the well system (106) being operated as a production well, the well system (106) may facilitate the extraction of hydrocarbons (or "production") from the reservoir (102).

In some embodiments disclosed herein, the well system (106) includes a rig (101), a wellbore (120), a data gathering and analysis system (160), and a well control system ("control system") (126). The well control system (126) may control various operations of the well system (106), such as well production operations, well drilling operation, well completion operations, well maintenance operations, and reservoir monitoring, assessment and development operations. In some embodiments, the well control system (126) includes a computer system.

The rig (101) is the machine used to drill a borehole to form the wellbore (120). Major components of the rig (101) include the drilling fluid tanks, the drilling fluid pumps (e.g., rig mixing pumps), the derrick or mast, the draw works, the rotary table or top drive, the drill string, the power generation equipment and auxiliary equipment. Drilling fluid, also referred to as "drilling mud" or simply "mud," is used to facilitate drilling boreholes into the earth, such as drilling oil and natural gas wells.

In some embodiments, a bottom hole assembly (BHA) (151) is attached to the drill string (150) to suspend into the wellbore (120) for performing the well drilling operation. The bottom hole assembly (BHA) is the lowest part of the drill string (150) and includes the drill bit, drill collar, stabilizer, mud motor, etc.

The wellbore (120) includes a bored hole (i.e., borehole) that extends from the surface (108) towards a target zone of the formation (104), such as the reservoir (102). The wellbore (120) may be drilled for exploration, development and production purposes. The wellbore (120) may facilitate the circulation of drilling fluids during drilling operations for the wellbore (120) to extend towards the target zone of the formation (104) (e.g., the reservoir (102)), facilitate the flow of hydrocarbon production (e.g., oil and gas) from the reservoir (102) to the surface (108) during production operations, facilitate the injection of substances (e.g., water) into the hydrocarbon-bearing formation (104) or the reservoir (102) during injection operations, or facilitate the communication of logging tools lowered into the formation (104) or the reservoir (102) during logging operations. The wellbore (120) may be logged by lowering a combination of physical sensors downhole to acquire data that measures various rock and fluid properties, such as irradiation, density, electrical and acoustic properties. The acquired data may be organized in a log format and referred to as well logs or well log data. In one or more embodiments, the wellbore (120) is a cased well where cement is injected into the annular space (122) between the well casing (121) and surrounding rock in the formation (104). The cement in the annular space (122) forms a cement sheath as a protective covering of the wellbore (120) in addition to the well casing (121). The cement sheath and the well casing (121) provide isolation between the borehole and surrounding rocks, referred to as zonal isolation. The concentric structure of the borehole, casing, cement, and surrounding rocks is referred to as the borehole setup, e.g., shown as borehole setup (123).

In some embodiments, the data gathering and analysis system (160) includes hardware and/or software with functionality for facilitating operations of the well system (106), such as well production operations, well drilling operation, well completion operations, well maintenance operations, and reservoir monitoring, assessment and development operations. For example, the data gathering and analysis system (160) may store and analyze computed tomography (CT) scan data of core samples to generate composite digital rock model and borehole digital model for simulating the borehole setup to predict cement longevity under various operations of the well system (106). While the data gathering and analysis system (160) is shown at a well site, embodiments are contemplated where at least a portion of the data gathering and analysis system (160) is located away from well sites. In some embodiments, the data gathering and analysis system (160) may include a computer system that is similar to the computing device (400) described below with regard to FIG. 4 and the accompanying description.

Figure 1B:
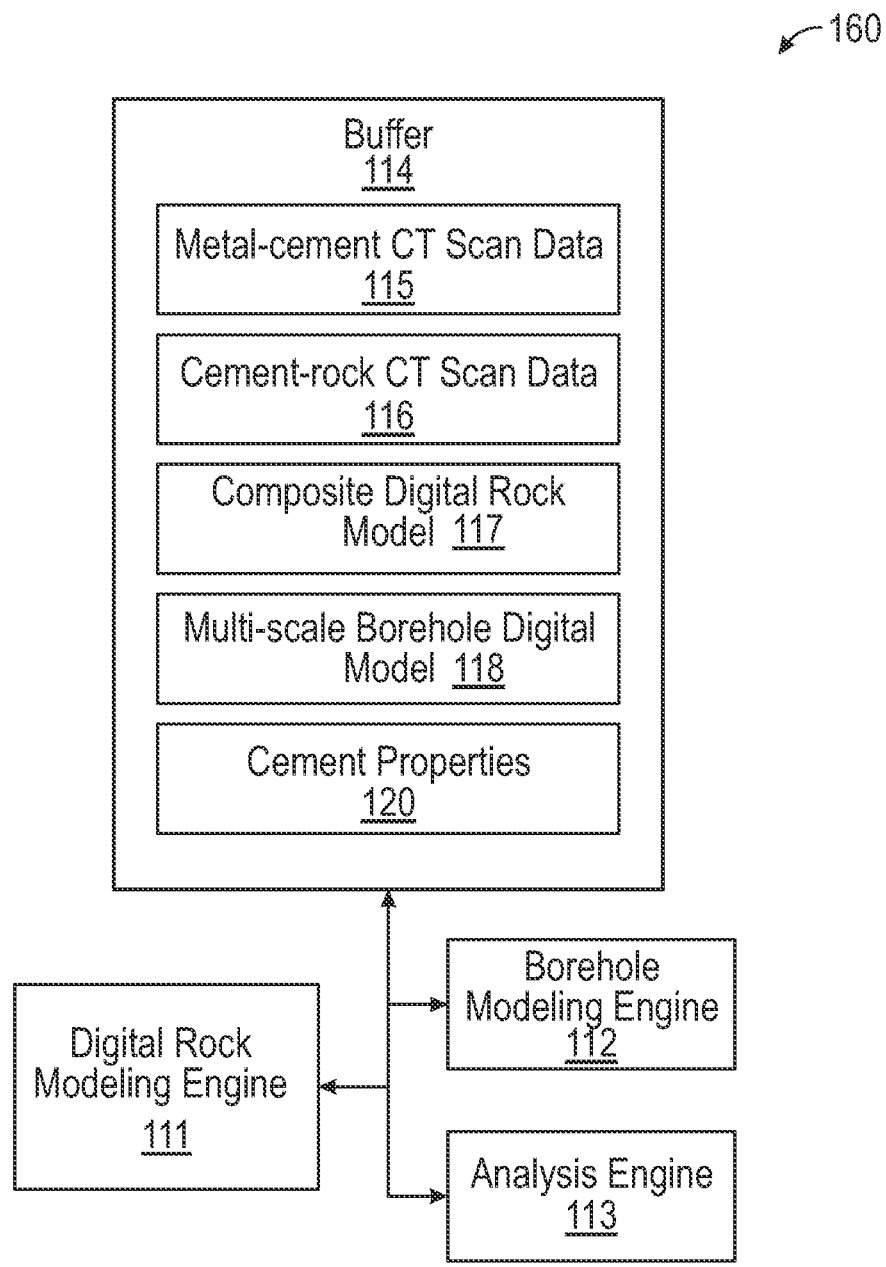

Turning to FIG. 1B, FIG. 1B shows a schematic diagram in accordance with one or more embodiments. Specifically, FIG. 1B illustrates details of the data gathering and analysis system (160) depicted in FIG. 1A above. In one or more embodiments, one or more of the modules and/or elements shown in FIG. 1B may be omitted, repeated, and/or substituted. Accordingly, embodiments of the invention should not be considered limited to the specific arrangements of modules and/or elements shown in FIG. 1B.

As shown in FIG. 1B, the data gathering and analysis system (160) has multiple components, including, for example, a buffer (111), a digital rock modeling engine (111), a borehole modeling engine (112), and an analysis engine (113). Each of these components (111, 112, 113) may be implemented in hardware (i.e., circuitry), software, or any combination thereof. Further, each of these components (111, 112, 113) may be located on the same computing device (e.g., personal computer (PC), laptop, tablet PC, smart phone, multifunction printer, kiosk, server, etc.) or on different computing devices connected by a network of any size having wired and/or wireless segments. In one or more embodiments, these components may be implemented using the computing device (400) described below in reference to computing device. Each of these components is discussed below.

In one or more embodiments of the invention, the buffer (111) may be any data structure that is configured to store metal-cement computed tomography (CT) scan data (115), cement-rock CT scan data (116), a composite digital rock model (117), a multi-scale borehole digital model (118), and cement properties (120). The metal-cement CT scan data (115) is the output data from a CT scan of a metal-cement core sample. The metal-cement core sample is a composite core sample having a metal section and a cement section adjoining each other. The cement-rock CT scan data (116) is the output data from a CT scan of a cement-rock core sample. The cement-rock core sample is a composite core sample having a cement section and a rock section adjoining each other. In these composite core samples, the metal section includes steel or other metal used to construct the wellbore casing, the cement section includes cement used to fill the annulus of the wellbore, and the rock section includes the rock surrounding the wellbore.

The composite digital rock model (117) is a computer model representing one or more physical properties of the metal-cement core sample, the cement-rock core sample, and/or a synthesized metal-cement-rock core sample. The composite digital rock model (117) includes grid cells each assigned with one or more data values to represent the one or more physical properties of the metal, cement, or rock at a corresponding location within the composite core sample. The composite digital rock model (117) includes labeled fields corresponding to minerals, structural pores, and other heterogenous elements of the composite core sample. The structural pores may exist in the metal, cement, or rock sections of the composite core sample. The multi-scale borehole digital model (118) is a computer model representing one or more physical properties of the metal-cement-rock sections of a borehole setup. The multi-scale borehole digital model (118) may be scaled up to any physical size of the borehole setup. The cement properties (120) are bulk properties (e.g., Young's modulus, Poisson's ratio, compressive strength, etc.) of cement that are computed at different pressure-temperature configurations.

In one or more embodiments of the invention, the digital rock modeling engine (111) is configured to analyze the metal-cement CT scan data (115) and cement-rock CT scan data (116) to generate 3D core sample images, to identify heterogeneous material segments (e.g., minerals, pores, etc.), and to generate the composite digital rock model (117) using digital rock physics (DRP) techniques. The borehole modeling engine (112) is configured to generate the multi-scale borehole digital model (118) by upscaling the composite digital rock model (117) to the physical size of the borehole setup. The analysis engine (113) is configured to compute bulk properties of metal, cement, and rock sections of the borehole setup using the multi-scale borehole digital model (118). The analysis engine (113) is further configured to generate and optimize a predicted cement longevity (i.e., time to failure) of the borehole setup under various borehole operation environments, and to facilitate performing a field operation in the borehole (120) using the predicted cement longevity.

In one or more embodiments, the digital rock modeling engine (111), the borehole modeling engine (112), and the analysis engine (113) perform the functions described above using the method flowchart described in reference to FIG. 2 below. An example of performing the method flowchart using the digital rock modeling engine (111), the borehole modeling engine (112), and the analysis engine (113) is described in reference to FIGS. 3A-3E below.

Although the data gathering and analysis system (160) is shown as having three components (111, 112, 113), in one or more embodiments of the invention, the data gathering and analysis system (160) may have more or fewer components. Furthermore, the functions of each component described above may be split across components or combined in a single component. Further still, each component (111, 112, 113) may be utilized multiple times to carry out an iterative operation.

Figure 2:
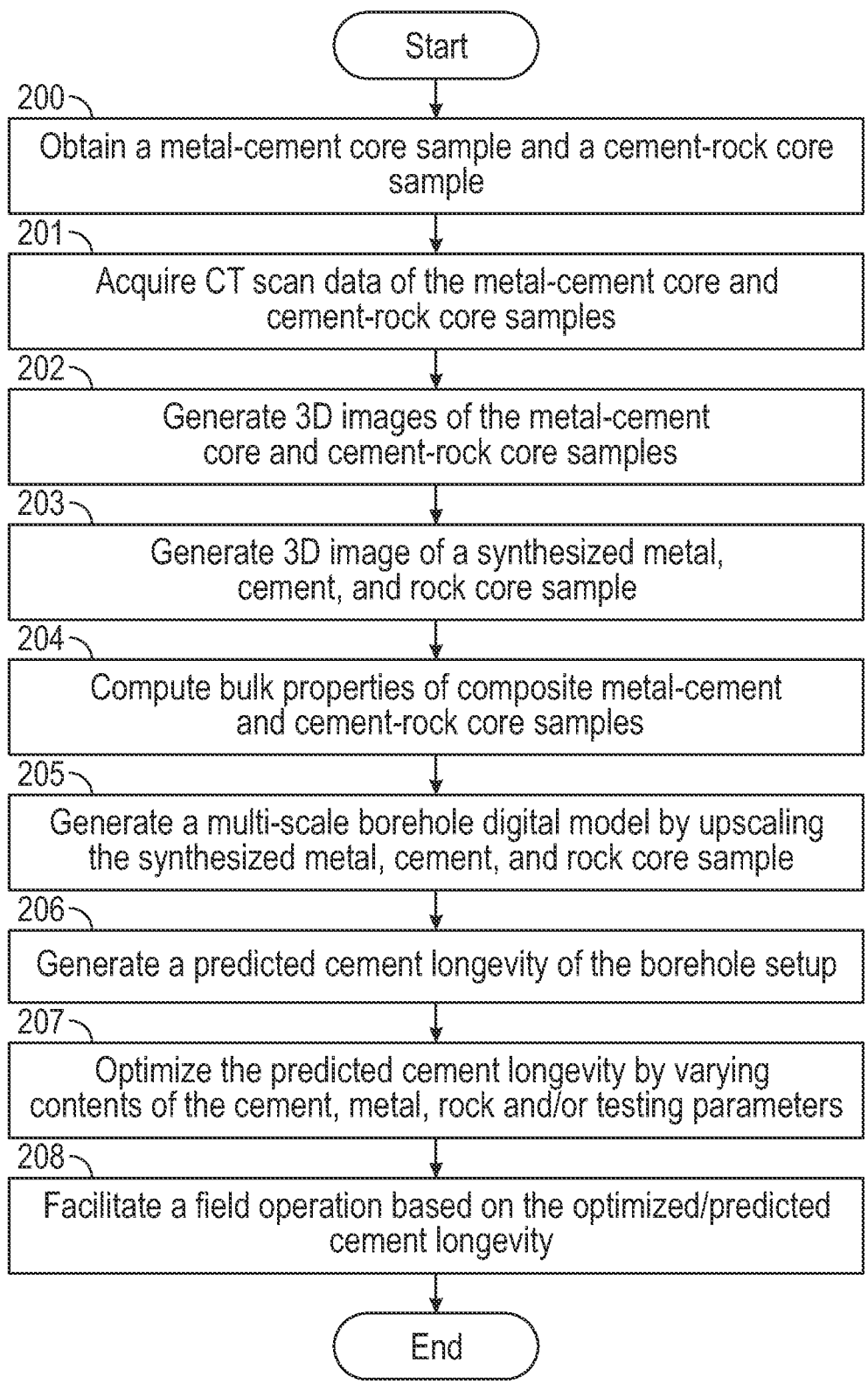
FIG. 2 shows a method flowchart in accordance with one or more embodiments.

FIG. 2 shows a flowchart in accordance with one or more embodiments disclosed herein. One or more of the steps in FIG. 2 may be performed by the components of the well environment (100), in particular the data gathering and analysis system (160), discussed above in reference to FIGS. 1A-1B. In one or more embodiments, one or more of the steps shown in FIG. 2 may be omitted, repeated, and/or performed in a different order than the order shown in FIG. 2. Accordingly, the scope of the disclosure should not be considered limited to the specific arrangement of steps shown in FIG. 2.

Referring to FIG. 2, initially in Step 200, sandstone and carbon steel core samples are obtained. For example, each core sample may be made of the same material as would be found in boreholes and may have a cylindrical shape with a diameter (D) measuring 0.2" and a height (H) measuring 0.5". A larger core sample may have a diameter measuring 2" and a height measuring 5". The sandstone core sample is obtained by coring at a wellsite. The carbon steel core sample is obtained from the material that is used to construct the wellbore casing at the wellsite. For example, 4140 carbon steel is used to form the core sample which is frequently used to build the casing oil well pipes. The cross sectional surfaces of the core samples are polished to control the roughness of the interface of a composite core sample. Cement is then mixed with water and cast on top of each core sample in a cylindrical mold to form a corresponding composite core sample having twice the height. The carbon steel core sample with casted cement on top forms the metal-cement core sample. The sandstone core sample with casted cement on top forms the cement-rock core sample. The molds may be cured at 180° F. and 3000 psi for 3 days.

In Step 201, computed tomography (CT) scan data of the composite core samples are acquired. The CT scan data may be acquired using a CT scanner in a laboratory associated with the wellsite. For the smaller size core sample (e.g., 0.2"D×FH), micro CT scan data at higher resolution (e.g., pixel dimension of 0.5 microns, 1 nanometer, etc.) are acquired over a core volume of approximately 0.15 mm on each side. For the larger core sample (e.g., 2"D×10"H), CT scan data at lower resolution (e.g., pixel dimension of 5 microns, 50 microns, etc.) are acquired. Both higher resolution and lower resolution CT scan data are used in constructing the digital rock model with high resolution CT scan data used in places of high variability and lower resolution CT scan data used in places of low variability.

In Step 202, the micro CT scan data of the metal-cement core sample and the micro CT scan data of the cement-rock core sample are imported and processed using CT image reconstruction software to generate 3D images of the composite core samples showing rock pores and other heterogeneous structures. For example, commercially available CT software based on Katsevich Filtered Back Projection (KFBP) image reconstruction algorithm may be used.

In Step 203, 3D images of the composite core samples generated from the CT micro scan data of the metal-cement core sample and cement-rock core sample are combined to construct a 3D image of a digital version of metal, cement, and rock core sample. For example, two 3D images are placed side by side to create a combined metal-cement-rock sample of twice the size. In one or more embodiments, an empty mesh of the combined sample is created where statistics algorithms (e.g., KFBP based CT software) are used to propagate the 3D images of the individual samples to create a combined sample. This can be made in KFBP but we used GeoDict software. In other words, the 3D image corresponds to a synthesized composite core sample of metal, cement, and rock that does not exist in the physical world.

In Step 204, bulk properties (e.g., Young's modulus, Poisson's ratio, compressive strength, etc.) of the composite metal-cement core sample, the cement-rock core sample, and the synthesized composite core sample of metal, cement, and rock are computed at different pressure-temperature configurations. The bulk properties are computed based on digital rock physics (DRP), e.g., using commercially available software such as GeoDict. As noted above, DRP is an image-based computational technique used to study the physical bulk properties of rocks. Image processing methods of DRP are used to segment various image components (e.g., minerals, pores, sand, steel, etc.) in the composite core sample and/or synthesized composite core sample into separate labeled fields for quantitative analyses. Each labeled field in the 3D images from image segmentation are assigned physical properties of the corresponding known material to generate a composite digital rock model. The composite digital rock model captures all the microstructural details of the real core sample material to serve as a data-driven model. The composite digital rock model is used to simulate physical processes, such as fluid flow, electrical currents, and elastic deformation of rocks using DRP techniques based on the basic laws of physics and numerical methods. In one or more embodiments, Steps 202, 203, and 204 are performed using the digital rock modeling engine (111) described in reference to FIG. 1B above.

In Step 205, a multi-scale borehole digital model is generated by upscaling the micro-scale composite core sample and/or synthesized composite core sample from Steps 203 and 204 above. The multi-scale borehole digital model may be generated to represent any physical size of the borehole setup. For example, the multi-scale borehole digital model may correspond to a casing/cement/borehole section of approximately 0.65 m on each side. Bulk properties (e.g., Young's modulus, Poisson's ratio, compressive strength, etc.) of the casing/cement/borehole sections at different pressure-temperature conditions are computed using DRP as in Step 204 above. In one or more embodiments, Step 205 is performed using borehole modeling engine (112) described in reference to FIG. 1B above.

In Step 206, the multi-scale borehole digital model generated in Step 205 is used to simulate physical processes, such as fluid flow, electrical currents, and elastic deformation of rocks in the casing/cement/borehole sections to generate a predicted cement longevity (i.e., time to failure) of the borehole setup under emulated well operation conditions. DRP techniques (e.g., GeoDict) are used to perform the simulation using the multi-scale borehole digital model.

In Step 207, an optimal value of the predicted cement longevity is calculated by repeating Steps 200-206 with varying contents of the cement, metal, rock and/or the testing parameters (e.g., pressure, temperature). The predicted cement longevity may be a numerical value e.g., a number of years or months. For example, Steps 200-206 may be repeatedly performed prior to drilling the borehole or constructing the casing such that the cased borehole is constructed based on optimal contents of the cement, metal, rock to achieve the optimized predicted cement longevity. In another example, Steps 200-206 may be repeatedly performed prior to initial borehole production such that the production operation is based on optimal pressure/temperature parameters to achieve the optimized predicted cement longevity.

In Step 208, a field operation is facilitated based on the optimized predicted cement longevity. For example, the wellbore completion operation may be performed based on the particular contents of the cement, metal, and rock that result in the optimized predicted cement longevity. In another example, the production operation may be performed based on the testing parameters (e.g., pressure, temperature) that result in the optimized predicted cement longevity. In yet another example, a wellbore maintenance operation may be scheduled and/or performed when the time since initial wellbore operation approaches the predicted cement longevity. In one or more embodiments, Steps 206, 207, and 208 are performed using the analysis engine (113) described in reference to FIG. 1B above.

FIGS. 3A-3E show an implementation example in accordance with one or more embodiments. The implementation example shown in FIGS. 3A-3E is based on the system and method flowchart described in reference to FIGS. 1A, 1B, and 2 above. In one or more embodiments, one or more of the modules and/or elements shown in FIGS. 3A-3E may be omitted, repeated, and/or substituted. Accordingly, embodiments disclosed herein should not be considered limited to the specific arrangements of modules and/or elements shown in FIGS. 3A-3E.

As noted above, laboratory testing of cement specimen under confining pressure may be performed to measure the material properties such as Young's modulus, Poisson's ratio and compressive strengths of the cement sheath. Analytical models based on the measured cement properties may be used to find when and approximately where cement may fail. For example, digital rock physics has been used to model the effective properties of rocks. Digital rock physics is an image-based computational technique used to study the physical properties of rocks. These models provide an idea of the failure instead of providing a full picture. In other words, merely modeling effective properties of rocks based on digital rock physics does not reveal whether the measured and/or modeled cement properties meet the longevity requirement for long term zonal isolation of the borehole setup of the well.

FIGS. 3A-3E show an example of an improved method for predicting cement longevity to assess the cement performance in the field before integrating the cement in or around a well. The example described below generates a composite digital rock model for the borehole setup from micro CT scan images of core samples. The composite digital rock model is validated through available data and used to model the integrity of the cement sheath and the risk of cement failure during different well operations. The effective cement properties of the composite digital rock model are simulated at a micro-scale using numerical methods based on physics and chemistry of metal, cement and rock. The simulations are upscaled to the borehole scale from the micro-scale to predict cement longevity under emulated well operations conditions.

Figure 3A:
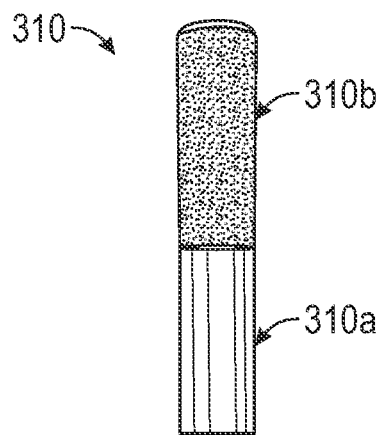
FIGS. 3A-3E show examples in accordance with one or more embodiments.

FIG. 3A shows an example metal-cement cylindrical sample (310) made of carbon steel (310a) and class G cement (310b). The metal-cement cylindrical sample (310) has a diameter of 0.2" and a height of 1" for acquiring a micro-CT scan image.

Figure 3B:
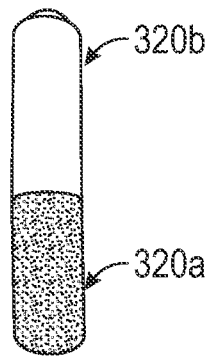

FIG. 3B shows an example rock-cement cylindrical sample (320) made of Berea sandstone (320a) and class G cement (320b). The rock-cement cylindrical sample (320) has a diameter of 0.2" and a height of 1" for acquiring a micro-CT scan image.

Figure 3C:
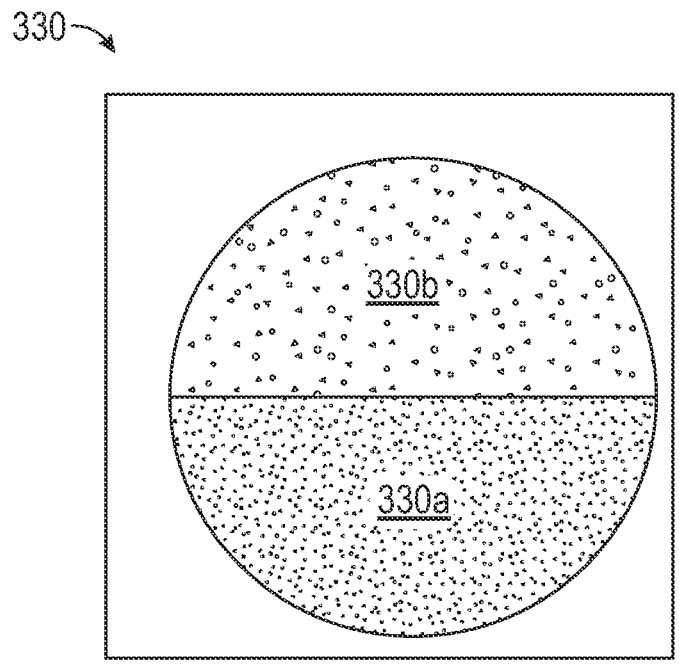

FIG. 3C shows an example CT scan image (330) of a larger rock-cement cylindrical sample. Note the difference in texture between the sandstone section (330a) and cement section (330b).

Figure 3D:
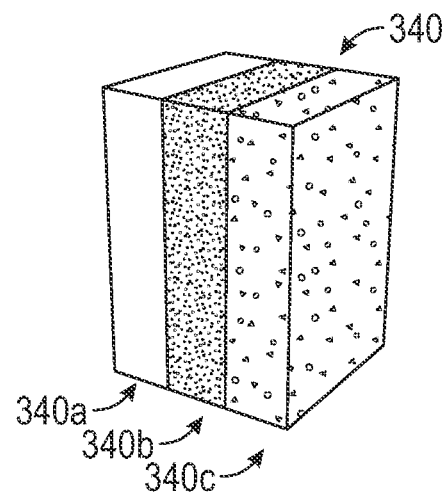

FIG. 3D shows an example 3D representation (340) of a digital metal-cement-rock (from left to right) sample at the micro-scale. The 3D representation (340) is referred to as a composite digital rock model (340) having a metal portion (340a), a cement portion (340b), and a rock portion (340c). Multiple composite digital rock models such as the composite digital rock model (340) are stacked and tiled up according to the geometry of a borehole to form a borehole digital model.

Figure 3E:
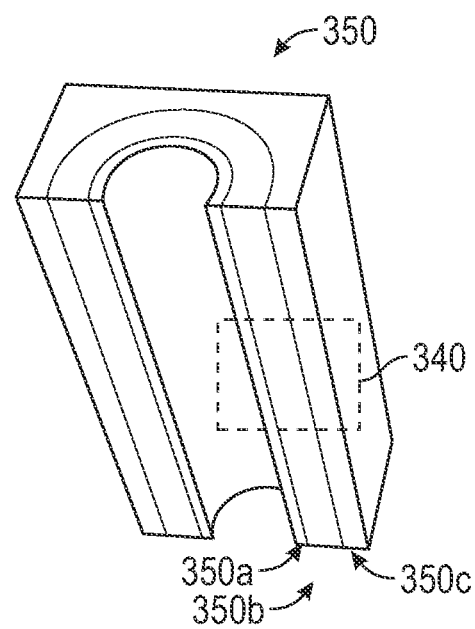

FIG. 3E shows an example 3D borehole digital model (350) of a borehole setup, such as the borehole setup (123) depicted in FIG. 1A above. The borehole digital model (350) consists of a collection of composite digital rock models (e.g., composite digital rock model (340)). In one or more embodiments, the borehole digital model (350) made of identical composite digital rock models that are replicated from the single composite digital rock model (340). Alternatively, the borehole digital model (350) may include different composite digital rock models having different cement-rock property values. The borehole digital model (350) is used to perform simulations to predict cement longevity under emulated well operation conditions. The borehole digital model (350) may be adjusted to model new cement additive chemistries to improve oil and gas well longevity. Because the borehole digital model (350) is an image-based model derived from real-life CT scan images of core samples, instead of an analytical model, the borehole digital model (350) is a better representation of the real phenomena. Being an image-based model, parallel processing, automation, AI and cloud computing may be employed using the borehole digital model (350) to achieve higher computing speed and lower computer memory requirements. Simulation results using the borehole digital model (350) provides details of the cement failure at the borehole setup at different snapshots of time, instead of merely approximate locations of failure.

Figure 4:
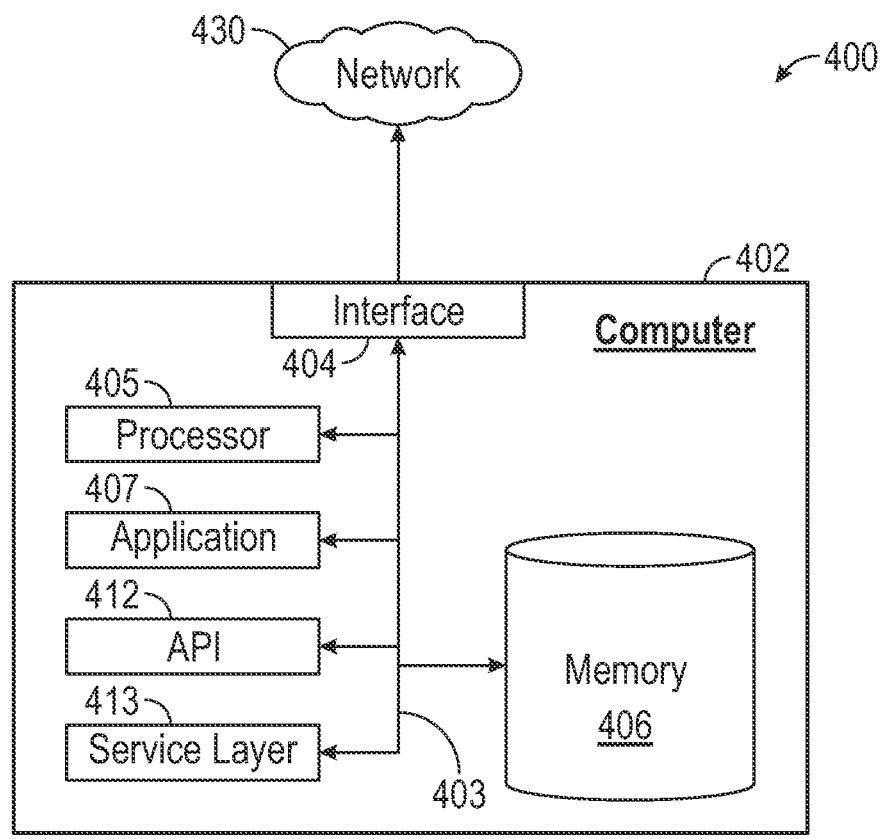
FIG. 4 shows a computing device in accordance with one or more embodiments.

Embodiments may be implemented on a computing device. FIG. 4 depicts a block diagram of a computing device (400) including a computer (402) used to provide computational functionalities associated with described machine learning networks, algorithms, methods, functions, processes, flows, and procedures as described in this disclosure, according to one or more embodiments. The illustrated computer (402) is intended to encompass any computing device such as a server, desktop computer, laptop/notebook computer, wireless data port, smart phone, personal data assistant (PDA), tablet computing device, one or more processors within these devices, or any other suitable processing device, including both physical or virtual instances (or both) of the computing device. Additionally, the computer (402) may include a computer that includes an input device, such as a keypad, keyboard, touch screen, or other device that can accept user information, and an output device that conveys information associated with the operation of the computer (402), including digital data, visual, or audio information (or a combination of information), or a GUI.

The computer (402) can serve in a role as a client, network component, a server, a database or other persistency, or any other component (or a combination of roles) of a computer system for performing the subject matter described in the instant disclosure. The illustrated computer (402) is communicably coupled with a network (430). In some implementations, one or more components of the computer (402) may be configured to operate within environments, including cloud-computing-based, local, global, or other environment (or a combination of environments).

At a high level, the computer (402) is an electronic computing device operable to receive, transmit, process, store, or manage data and information associated with the described subject matter. According to some implementations, the computer (402) may also include or be communicably coupled with an application server, e-mail server, web server, caching server, streaming data server, business intelligence (BI) server, or other server (or a combination of servers).

The computer (402) can receive requests over network (430) from a client application (for example, executing on another computer (402)) and responding to the received requests by processing the said requests in an appropriate software application. In addition, requests may also be sent to the computer (402) from internal users (for example, from a command console or by other appropriate access method), external or third-parties, other automated applications, as well as any other appropriate entities, individuals, systems, or computers.

Each of the components of the computer (402) can communicate using a system bus (403). In some implementations, any or all of the components of the computer (402), both hardware or software (or a combination of hardware and software), may interface with each other or the interface (404) (or a combination of both) over the system bus (403) using an application programming interface (API) (412) or a service layer (413) (or a combination of the API (412) and service layer (413). The API (412) may include specifications for routines, data structures, and object classes. The API (412) may be either computer-language independent or dependent and refer to a complete interface, a single function, or even a set of APIs. The service layer (413) provides software services to the computer (402) or other components (whether or not illustrated) that are communicably coupled to the computer (402). The functionality of the computer (402) may be accessible for all service consumers using this service layer. Software services, such as those provided by the service layer (413), provide reusable, defined business functionalities through a defined interface. For example, the interface may be software written in JAVA, C++, or other suitable language providing data in extensible markup language (XML) format or another suitable format. While illustrated as an integrated component of the computer (402), alternative implementations may illustrate the API (412) or the service layer (413) as stand-alone components in relation to other components of the computer (402) or other components (whether or not illustrated) that are communicably coupled to the computer (402). Moreover, any or all parts of the API (412) or the service layer (413) may be implemented as child or sub-modules of another software module, enterprise application, or hardware module without departing from the scope of this disclosure.

The computer (402) includes an interface (404). Although illustrated as a single interface (404) in FIG. 4, two or more interfaces (404) may be used according to particular needs, desires, or particular implementations of the computer (402). The interface (404) is used by the computer (402) for communicating with other systems in a distributed environment that are connected to the network (430). Generally, the interface (404) includes logic encoded in software or hardware (or a combination of software and hardware) and operable to communicate with the network (430). More specifically, the interface (404) may include software supporting one or more communication protocols, such as the Wellsite Information Transfer Specification (WITS) protocol, associated with communications such that the network (430) or interface's hardware is operable to communicate physical signals within and outside of the illustrated computer (402).

The computer (402) includes at least one computer processor (405). Although illustrated as a single computer processor (405) in FIG. 4, two or more processors may be used according to particular needs, desires, or particular implementations of the computer (402). Generally, the computer processor (405) executes instructions and manipulates data to perform the operations of the computer (402) and any algorithms, methods, functions, processes, flows, and procedures as described in the instant disclosure.

The computer (402) also includes a memory (406) that holds data for the computer (402) or other components (or a combination of both) that can be connected to the network (430). For example, memory (406) can be a database storing data consistent with this disclosure. Although illustrated as a single memory (406) in FIG. 4, two or more memories may be used according to particular needs, desires, or particular implementations of the computer (402) and the described functionality. While memory (406) is illustrated as an integral component of the computer (402), in alternative implementations, memory (406) can be external to the computer (402).

The application (407) is an algorithmic software engine providing functionality according to particular needs, desires, or particular implementations of the computer (402), particularly with respect to functionality described in this disclosure. For example, application (407) can serve as one or more components, modules, applications, etc. Further, although illustrated as a single application (407), the application (407) may be implemented as multiple applications (407) on the computer (402). In addition, although illustrated as integral to the computer (402), in alternative implementations, the application (407) can be external to the computer (402).

There may be any number of computers (402) associated with, or external to, a computer system containing a computer (402), wherein each computer (402) communicates over network (430). Further, the term "client," "user," and other appropriate terminology may be used interchangeably as appropriate without departing from the scope of this disclosure. Moreover, this disclosure contemplates that many users may use one computer (402), or that one user may use multiple computers (402).

While the invention has been described with respect to a limited number of embodiments, those skilled in the art, having benefit of this disclosure, will appreciate that other embodiments can be devised which do not depart from the scope of the disclosure as disclosed herein. Accordingly, the scope of the disclosure should be limited only by the attached claims.

What is claimed:

1. A method to perform a field operation with digital cement modeling, comprising:

acquiring computed tomography (CT) scan data of a metal-cement core sample and a cement-rock core sample that are associated with a borehole;

generating, based on the CT scan data of the metal-cement core sample and the cement-rock core sample, a three-dimensional (3D) image of a synthesized metal, cement, and rock core sample;

identifying, in the 3D image, structural pores and heterogeneous material segments in each of a metal section, cement section, and rock section of the synthesized metal, cement, and rock core sample, wherein the heterogeneous material segments comprise minerals, sand, and steel;

generating, by at least assigning corresponding physical properties to the heterogeneous material segments in the 3D image, a composite digital rock model, wherein the physical properties comprise Young's modulus, Poisson's ratio, and compressive strength of the minerals, sand, and steel;

generating, by at least upscaling the synthesized metal, cement, and rock core sample according to a geometry of the borehole, a multi-scale borehole digital model of the borehole;

simulating, using the multi-scale borehole digital model, a well operation condition of the borehole at different time points to generate a predicted time to cement failure, wherein the cement failure corresponds to when simulated elastic deformation in the cement section exceeds a limit based on the compressive strength in the cement section; and facilitating, based on the predicted time to cement failure, the field operation.

2. The method of claim 1, further comprising:
constructing the metal-cement core sample by casting a cement section on top of a metal core sample,
wherein the metal core sample comprises metal material used to construct a borehole casing of the borehole setup, and
wherein the cement section comprises cement material used to fill an annulus of the borehole setup.

3. The method of claim 1, further comprising:
constructing the cement-rock core sample by casting a cement section on top of a rock core sample,
wherein the cement section comprises cement material used to fill an annulus of the borehole setup, and
wherein the rock core sample comprises rock material surrounding the borehole setup.

4. The method of claim 1, further comprising:
optimizing the predicted cement longevity by varying contents of metal material, cement material, rock material of the metal-cement core sample and the cement-rock core sample, and an operating condition of the borehole setup,
wherein the predicted cement longevity is generated based on applying the digital rock physics techniques to the multi-scale borehole digital model under the operating condition of the borehole setup.

5. The method of claim 1, further comprising:
wherein the multi-scale borehole digital model is generated by replicating the composite digital rock model.

6. The method of claim 5, further comprising:
computing bulk mechanical properties of the borehole setup based on the structural pores and heterogeneous material segments of the multi-scale borehole digital model.

7. The method of claim 1,
wherein the field operation comprises at least one of a well production operation, well drilling operation, well completion operation, and well maintenance operation.

8. A data gathering and analysis system, comprising:
a data storage device comprising memory for storing computed tomography (CT) scan data of core samples, core sample images, and borehole digital models;
a computer processor; and
the memory further storing instructions, when executed, causing the computer processor to:
  acquire the CT scan data of a metal-cement core sample and a cement-rock core sample that are associated with a borehole;
  generate, based on the CT scan data of the metal-cement core sample and the cement-rock core sample, a three-dimensional (3D) image of a synthesized metal, cement, and rock core sample;
  identify, in the 3D image, structural pores and heterogeneous material segments in each of a metal section, cement section, and rock section of the synthesized metal, cement, and rock core sample, wherein the heterogeneous material segments comprise minerals, sand, and steel;
  generate, by at least assigning corresponding physical properties to the heterogeneous material segments in the 3D image, a composite digital rock model, wherein the physical properties comprise Young's modulus, Poisson's ratio, and compressive strength of the minerals, sand, and steel;
  generate, by at least upscaling the synthesized metal, cement, and rock core sample according to a geometry of the borehole, a multi-scale borehole digital model of the borehole;
  simulate, using the multi-scale borehole digital model, a well operation condition of the borehole at different time points to generate a predicted time to cement failure, wherein the cement failure corresponds to when simulated elastic deformation in the cement section exceeds a limit based on the compressive strength in the cement section; and
  facilitate, based on the predicted time to cement failure, the field operation.

9. The data gathering and analysis system of claim 8,
wherein the metal-cement core sample is constructed by casting a cement section on top of a metal core sample,
wherein the metal core sample comprises metal material used to construct a borehole casing of the borehole setup, and
wherein the cement section comprises cement material used to fill an annulus of the borehole setup.

10. The data gathering and analysis system of claim 8,
wherein the cement-rock core sample is constructed by casting a cement section on top of a rock core sample,
wherein the cement section comprises cement material used to fill an annulus of the borehole setup, and
wherein the rock core sample comprises rock material surrounding the borehole setup.

11. The data gathering and analysis system of claim 8, the instructions, when executed, further causing the computer processor to:
optimize the predicted cement longevity by varying contents of metal material, cement material, rock material of the metal-cement core sample and the cement-rock core sample, and an operating condition of the borehole setup,
wherein the predicted cement longevity is generated based on applying the digital rock physics techniques to the multi-scale borehole digital model under the operating condition of the borehole setup.

12. The data gathering and analysis system of claim 8,
wherein the multi-scale borehole digital model is generated by replicating the composite digital rock model.

13. The data gathering and analysis system of claim 12, the instructions, when executed, further causing the computer processor to:
compute bulk mechanical properties of the borehole setup based on the structural pores and heterogeneous material segments of the multi-scale borehole digital model.

14. The data gathering and analysis system of claim 8,
wherein the field operation comprises at least one of a well production operation, well drilling operation, well completion operation, and well maintenance operation.

15. A system comprising:
a wellsite having a borehole penetrating a subterranean formation in a field; and
a data gathering and analysis system comprising:
  a processor; and
  memory storing instructions, when executed by the computer processor comprising functionality for:
    acquiring computed tomography (CT) scan data of a metal-cement core sample and a cement-rock core sample that are associated with a borehole;
    generating, based on the CT scan data of the metal-cement core sample and the cement-rock core sample, a three-dimensional (3D) image of a synthesized metal, cement, and rock core sample;
    identifying, in the 3D image, structural pores and heterogeneous material segments in each of a metal section, cement section, and rock section of the synthesized metal, cement, and rock core sample, wherein the heterogeneous material segments comprise minerals, sand, and steel;
    generating, by at least assigning corresponding physical properties to the heterogeneous material segments in the 3D image, a composite digital rock model, wherein the physical properties comprise Young's modulus, Poisson's ratio, and compressive strength of the minerals, sand, and steel;
    generating, by at least upscaling the synthesized metal, cement, and rock core sample according to a geometry of the borehole, a multi-scale borehole digital model of the borehole;
    simulating, using the multi-scale borehole digital model, a well operation condition of the borehole at different time points to generate a predicted time to cement failure, wherein the cement failure corresponds to when simulated elastic deformation in the cement section exceeds a limit based on the compressive strength in the cement section; and
    facilitating, based on the predicted time to cement failure, the field operation.

16. The system of claim 15,
wherein the metal-cement core sample is constructed by casting a first cement section on top of a metal core sample,
wherein the cement-rock core sample is constructed by casting a second cement section on top of a rock core sample,
wherein the metal core sample comprises metal material used to construct a borehole casing of the borehole setup, wherein the first and second cement sections comprise cement material used to fill an annulus of the borehole setup, and wherein the rock core sample comprises rock material surrounding the borehole setup.

17. The system of claim 16, the data gathering and analysis system further comprising functionality for:

optimizing the predicted cement longevity by varying contents of the metal material, the cement material, the rock material, and an operating condition of the borehole setup, wherein the predicted cement longevity is generated based on applying the digital rock physics techniques to the multi-scale borehole digital model under the operating condition of the borehole setup.

18. The system of claim 15, wherein the multi-scale borehole digital model is generated by replicating the composite digital rock model.

19. The system of claim 18, the data gathering and analysis system further comprising functionality for:

computing bulk mechanical properties of the borehole setup based on the structural pores and heterogeneous material segments of the multi-scale borehole digital model.

20. The system of claim 15, wherein the field operation comprises at least one of a well production operation, well drilling operation, well completion operation, and well maintenance operation.

* * * * *